United States Patent [19]

Ho et al.

[11] Patent Number: 4,466,879
[45] Date of Patent: Aug. 21, 1984

[54] POLAROGRAPHIC OXYGEN SENSOR

[75] Inventors: Nelson Ho, Murray; Bryan Thompson; Jiri Kratochvil, both of Sandy, all of Utah

[73] Assignee: Critikon, Inc., Tampa, Fla.

[21] Appl. No.: 483,336

[22] Filed: Apr. 8, 1983

Related U.S. Application Data

[63] Continuation of Ser. No. 262,091, May 11, 1981, abandoned.

[51] Int. Cl.³ .............................................. G01N 27/46
[52] U.S. Cl. ...................................... 204/415; 204/1 T
[58] Field of Search ................................ 204/1 P, 415

[56] References Cited

U.S. PATENT DOCUMENTS

| | | | |
|---|---|---|---|
| 3,088,905 | 5/1963 | Glover | 204/415 |
| 3,303,085 | 2/1967 | Price et al. | 428/131 |
| 3,394,069 | 7/1968 | Solomons | 204/415 |
| 3,415,730 | 12/1968 | Haddad | 204/415 |
| 3,518,179 | 6/1970 | Bleak et al. | 204/415 |
| 3,700,579 | 10/1972 | Clifton et al. | 204/415 |
| 3,794,575 | 2/1974 | Niedrach et al. | 204/415 |
| 3,826,730 | 7/1974 | Watanabe et al. | 204/415 |
| 3,912,614 | 10/1975 | Spracklen et al. | 204/415 |
| 3,948,745 | 4/1976 | Guilbault et al. | 204/415 |
| 4,197,852 | 4/1980 | Schindler et al. | 204/415 |

Primary Examiner—T. Tung
Attorney, Agent, or Firm—Audley A. Ciamporcero, Jr.

[57] ABSTRACT

A polarographic sensor for blood oxygen monitoring is defined by respective anode and cathode electrode wires fixedly maintained in conventional fashion. The end cross sections of the wires are carried on a surface, and overlying this surface is a capillary pore ultrafiltration membrane. The microscopic capillary pores, which have diameters less than 12 micrometers each, pass water therethrough and thus allow the blood, which passes on the side of the membrane opposite the anode and cathode, to act as its own electrolyte.

6 Claims, 4 Drawing Figures

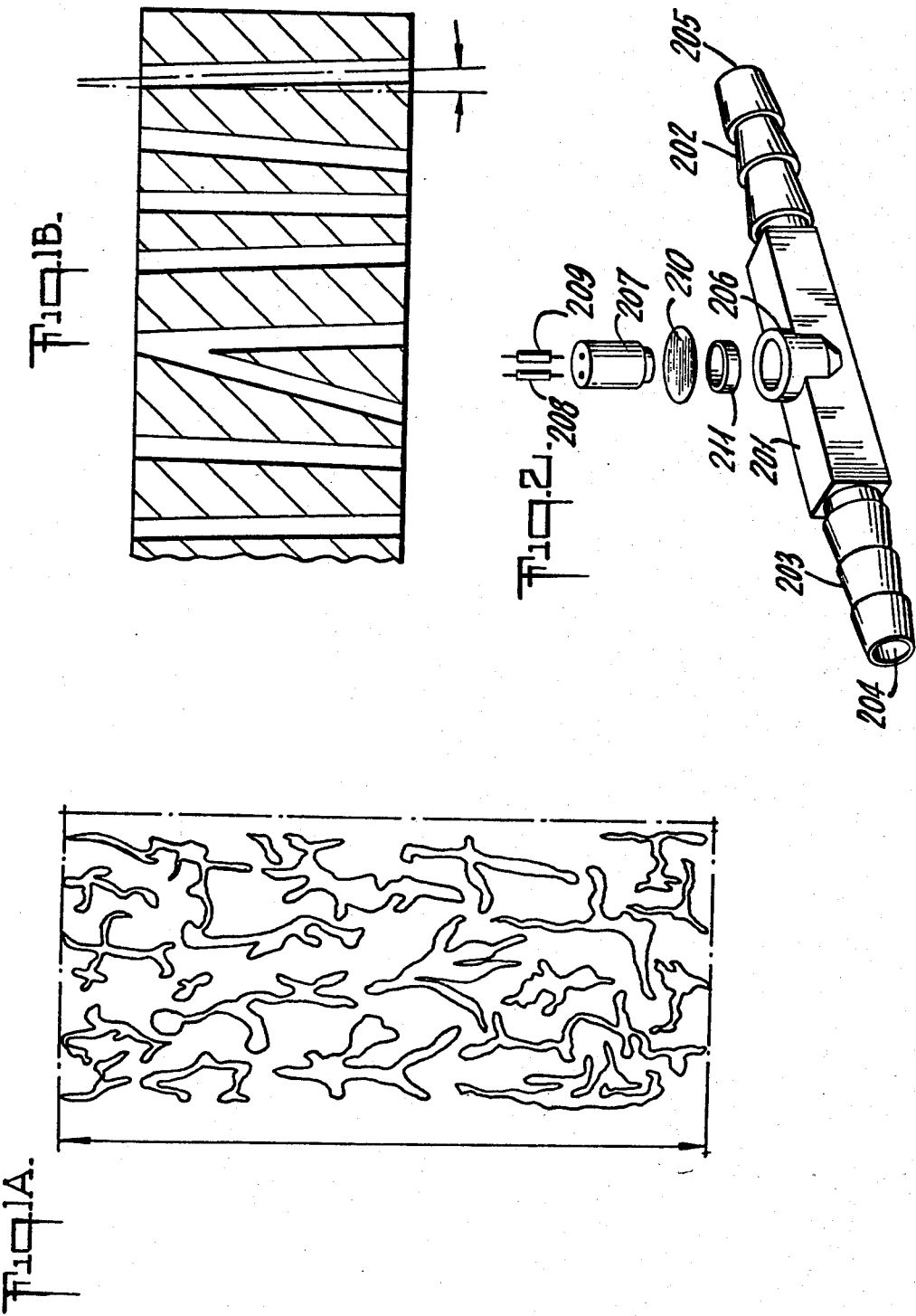

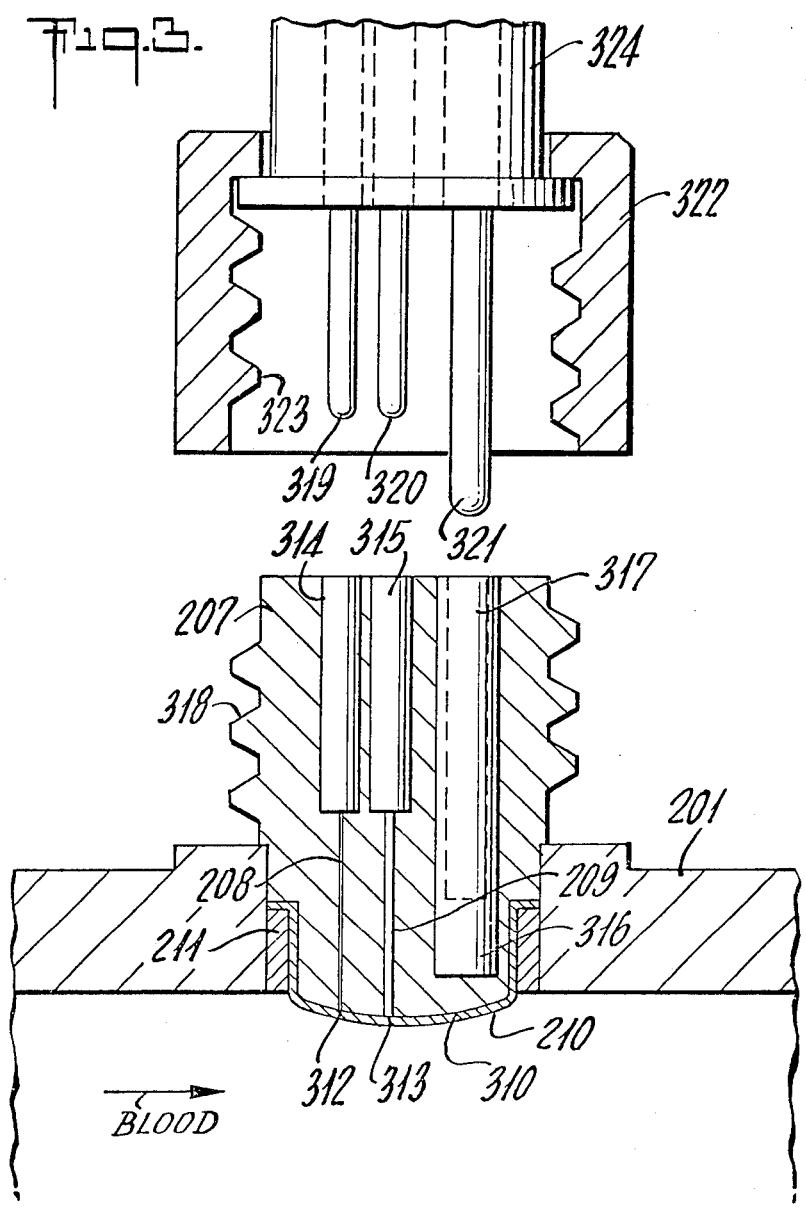

4,466,879

POLAROGRAPHIC OXYGEN SENSOR

This is a continuation of application Ser. No. 262,091, filed May 11, 1981 now abandoned.

FIELD OF THE INVENTION

This invention relates to polarographic electrodes, and more particularly to novel polarographic electrode structures for monitoring and determining blood oxygen partial pressure.

BACKGROUND OF THE INVENTION AND PRIOR ART

Polarographic electrodes have been found to be an invaluable tool for measuring the partial pressure of oxygen in blood ($pO_2$) in extracorporeal loops such as those utilized during surgery. Numerous publications and patents have dealt with these electrodes, ever seeking designs which are reliable, rugged, and simple to manufacture. For a rather exhaustive treatment of the theory of oxygen electrode operation, and a presentation of most of the well known prior art designs, see "Medical and Biological Applications of Electrochemical Devices", Chapter 6, Edt. by J. Koryta, John Wiley & Sons Limited, 1980.

In its simplest form, a polarographic oxygen electrode consists of a noble metal cathode immersed in the solution to be monitored, and negatively biased with respect to a reference electrode (i.e. anode) which also is coupled to the solution. Oxygen content of the sample is measured amperometrically at the potential of the limiting current, at which point the oxygen vs. current characteristic defines a linear proportionality between oxygen content and electrical current.

Early work in the polarographic electrode field concerned protection of the metallic electrode system from surface contamination and poisoning by blood proteins. A watershed in this area occurred in a 1956 disclosure by L. C. Clark, Jr. (Trans. American Society Art. Int. Organs, Vol. 2, pp. 41–45, 1956), involving an entirely closed system wherein a cathode, an anode, and an electrolyte are physically separated from the solution to be measured by a hydrophobic membrane which is permeable only by the gas (e.g., oxygen) to be measured. See also U.S. Pat. No. 2,913,386 to Clark, issued Nov. 17, 1959, and U.S. Pat. No. 3,826,730 to Watanabe et al., issued July 30, 1974.

More recently, sensors have been developed which utilize a hydrophilic, rather than hydrophobic membrane to enclose the anode-cathode-electrolyte cell. Such sensors utilize membranes which are permeable not only by blood gases, but also by water and blood plasma electrolytes; they are not, however, permeable by proteins or other large molecules. Examples of hydrophilic materials known to be applicable in such cells are collodion, cellophane, polystyrene, "hydron", and the like. See, for example, the thesis of D. W. DeHaas, Rotterdam (1977), setting forth a sensor utilizing the membrane material commercially available under the trade name pHEMA (poly [2-hydroxyethyl methacrylate]).

Based on the foregoing precepts, other variants have been disclosed. For example, U.S. Pat. No. 3,700,579 to Clifton et al. discloses utilization of the water absorption characteristics of chlorinated fluorocarbon materials to employ them as membrane materials. Similar thinking has led to the use of tortuous pore membranes prepared from mixed esters of cellulose.

Each of the foregoing approaches to the design of polarographic sensors involves rather severe drawbacks. Moreover, though the physical and dynamic mechanisms are different for each, substantially all have problems relating to electrical drift and instability, poor reusability characteristics, poor mechanical strength, difficulties of calibration, and excessive complexity of construction. pHEMA membranes are subject to degradation by hydroxyl ions generated during the electro reduction of oxygen in the sensor. Membranes based on chlorinated fluorocarbon materials (e.g. polytetrafluoroethylene) must be activated by forcing aqueous solution into the polymeric matrix by steam sterilization. Even so, such sensors are generally sensitive to osmotic effects. Cellulosic membranes stretch when fully hydrated, leading to changes in electrolyte dimension and consequent sensor instability. Furthermore, glycerin, which is added to the membrane during manufacture to achieve requisite flexibility, leaches out of the membrane during first use. Redrying of the previously hydrated membrane yields a very brittle material, lacking not only mechanical strength, but in any event making it substantially impossible to precalibrate.

It is a primary object of the present invention to provide a polarographic oxygen sensor design and construction which substantially improves upon the previously characterized prior art approaches, substantially eliminating or at least vastly decreasing prior art problems of structural complexity, electrical instability, membrane strength, and the like. More specific objects of the present invention include providing a sensor construction and membrane selection characterized by rapid hydration, resistance to chemical degradation or alteration during the sensing process, physical and mechanical stability, compatibility with blood, precalibration facility, and rapidity of response.

SUMMARY OF THE INVENTION

In accordance with the principles of the present invention, the anode and cathode electrodes of a polarographic sensor are separated from the blood by a membrane, but in view of the nature of the membrane to be utilized, the blood itself effectively acts as the electrolyte. In particular, in accordance with the principles of the present invention, a polarographic electrode employs a capillary pore ultrafiltration membrane directly overlying and contacting the surface carrying the anode and cathode electrodes. In particular, such membrane defines therein cylindrical, substantially linear ultrafiltration passageways having a diameter of less than 12 micrometers, whereby fluid and gases from the blood pass directly and quickly through the membrane to act as a self-provided electrolyte, but proteins and the like large particles can neither penetrate nor substantially block the pores.

Preferred compositions of the membrane material include polycarbonate and polyester, both of which may be processed in accordance with the methods set forth in U.S. Pat. No. 3,303,085 to Price et al. to produce the requisite capillary pore ultrafiltration structure. Pore density in the range up to $6 \times 10^9$ pores per square centimeter is suitable.

It is noteworthy that such membranes hydrate in less than 10 minutes' time, are neither degraded nor chemically altered by the polarographic reaction, are blood compatible and physically and mechanically stable when wet, and are quite thermally stable and mechanically rugged.

DESCRIPTION OF THE DRAWINGS

FIGS. 1A and 1B show microscopic views of respective cellulosic tortuous and capillary pore membrane structures. FIG. 2 shows an exploded view of an illustrative embodiment of an oxygen sensor employing the principles of the present invention; and FIG. 3 shows a cutaway view of a preferred embodiment of the principles of the present invention.

BEST MODE FOR CARRYING OUT THE INVENTION

As stated hereinbefore, preferred forms of the principles of the present invention use capillary pore ultrafiltration membranes. As the term is utilized herein, a capillary pore ultrafiltration membrane is one in which a sheet like body of film or material is penetrated therethrough by substantially straight, substantially cylindrical passageways or pores of reasonably uniform and predictable dimension and density. Such membranes of polycarbonate and polyester composition, among others, are commercially available, having pore size and pore density suitable for application in accordance with the principles of the present invention. Additionally, U.S. Pat. No. 3,303,085 to Price et al., issued Feb. 7, 1967, and entitled "Molecular Sieves and Methods for Producing Same" discloses an advantageous approach to production of capillary pore ultrafiltration membranes. Briefly, in accordance with the Price et al. patent, the film sheets are exposed to collimated charged particles in a nuclear reactor. As the particles pass through the material they leave sensitized tracks, which upon conduct of an etching process, are cleared to form cylindrical pores. Careful control of the timing of the etching process results in corresponding control of pore size.

The physical and structural difference between capillary pore ultrafiltration membranes, and the more common cellulosic tortuous pore membrane, may be seen by comparing FIGS. 1A and 1B. In particular, FIG. 1A shows in cross section a microscopic (i.e. approximately 150 micrometers in the vertical, or thickness dimension) cross section of a cellulosic tortuous pore membrane. It will be seen that such membrane defines irregular, maze like structure. By comparison, FIG. 1B shows a microscopic cross section view (in the range of 10 micrometers in the vertical thickness dimension) useful in accordance with the principles of the present invention. It will be seen that the capillary pore ultrafiltration membrane of FIG. 1B defines very uniform pores or passageways therethrough (i.e. "straight through"), the overwhelming percentage of which divert less than 10 degrees from the normal. Such membranes are commercially available having up to six billion pores per square centimeter, although preferred embodiments of the principles of the present invention employ such membranes having 20 to 30 million pores per square centimeter. Likewise, the diameter of the pores may range up to 15 micrometers, but preferred embodiments of the principles of the present invention utilize membranes having a pore size in the range of 0.1 to 0.5 micrometers. It will be appreciated that such dimensional constraints readily permit water, blood plasma, blood gas molecules, and the like to penetrate the pores, but do not permit proteins or the like large molecules to pass through or lodge themselves into the pores.

Referring next to FIG. 2, there is shown an illustrative embodiment of the principles of the present invention, adapted to sense oxygen partial pressure in an extracorporeal loop. In FIG. 2, a housing 201 defines a flow path between respective inlet and outlet ports 204 and 205, through which blood in the extracorporeal loop is permitted to flow. Couplings 202 and 203 facilitate connection of the housing 201 to tubings or sleeves defining the blood loop. Sensing occurs in a central region of the housing 201, where there is defined a cylindrical collar or sleeve 206 which penetrates the housing 201 into the blood passageway between ports 204 and 205. An assembly consisting of a sensor body 207, membrane 210, and retaining ring 211, suitably also provided with cathode 208 and anode 209 electrode wire assemblies, is mounted within the collar or sleeve 206, with the membrane 210 being drawn over the lower portion of sensor body 207 and held there by the retaining ring 211. Hence, the membrane 210, which is a capillary pore membrane of the sort previously described and depicted in conjunction with FIG. 1B, is carried adjacent the passageway between ports 204 and 205, so that blood passing through the housing 201 flows across the membrane 210 (i.e. the side opposite the one which is in contact with the sensor body 207 and the cathode 208 and anode 209 electrode assemblies).

For a clearer and more detailed understanding of the principles of the present invention, reference may be had to FIG. 3, which depicts a more detailed construction of a polarographic sensor embodying the principles of the present invention. The embodiment of FIG. 3 defines a cable assembly (e.g. 322, 324, etc.), and a sensor assembly (201, 207, etc.) which when electrically and physically joined together, provide oxygen monitoring in accordance with the principles of the present invention.

With first reference to the cable assembly, which, it is understood, will be reusable with different sensor assemblies, a cathode pin 319, an anode pin 320, and a thermistor housing 321 protrude outwardly from a cable mechanism 324. It will be understood that the cable mechanism 324 extends back to suitable electronics and/or utilization apparatus, whereby electrical signals from the respective pins 319 and 320 and from a thermistor located within the housing 321, may be processed to yield data in the form of blood gas concentrations.

A rotatable lock nut 322 defines a female threaded portion 323 to allow the cable assembly to be physically and hence securely electrically coupled to a sensor assembly in accordance with the principles of the present invention.

The lower portion of FIG. 3 defines a sensor assembly, with the housing 201 being cut away, it being understood that blood flow occurs in the channel therebeneath, as shown. As will be noted from the cross sectional view of FIG. 3, the sensor body 207 has respective conductive recesses 314 and 315 to receive, respectively, the cathode pin 319 and the anode pin 320 of the cable assembly. In preferred form, these conductive recesses 314 and 315 are defined by metallic sleeves which snugly contain the pins 319 and 320 in physical and electrical contact. Beneath the sleeve portions 314 and 315 for receipt of the pins 319 and 320, the cathode and anode assemblies of the sensor constitute narrow, wirelike formations 208 and 209, which have terminal cross sections 312 and 313, respectively smoothly faced on the lower surface 310 of the sensor body 207. As in the case of prior art sensors, the active area of the cathode 208 and anode 209 wires, in particular cross sections 312 and 313 thereof, respectively, constitute the actual active electrodes of the sensor. The sensor body 207, and hence also the balance of lowermost surface 310, is made from a material which plays no active role in the polarographic sensing process.

The sensor assembly also defines therein an insert sleeve 317 for receiving the thermistor housing 321 of the cable assembly. Such fit is thermally conductive and physically snug, such that thermal energy from a heat sink 316 in the sensor body 207 passes substantially directly and freely to the thermistor within housing 321. This thermoelectric information from thermistor 321 via heat sink 316 is utilized in conventional fashion to temperature compensate the amperometric information conveyed via the anode and cathode assemblies.

It will be appreciated that the sensor assembly defines on its outer surface a male threaded portion 318 which is matable with the female threaded portion 323 of lock nut 322, whereby the cable assembly may be installed on the center assembly by respective interconnections of the cathode, anode, and thermistor aspects of cable and sensor assemblies, and a tightening of the lock nut 322 upon the sensor body 207.

In accordance with the principles of the present invention, the capillary pore ultrafiltration membrane 210 is drawn directly over the surface 310, and hence also over the active portions 312 and 313 of the cathode 208 and anode 209 wires, and is held there by a retaining ring 211. It will be appreciated that those of ordinary skill in the art may desire to hold the periphery of the membrane 210 in place by other means, for example by sonic, thermal, or chemical bonding methods. In any event, the membrane 210 is held against the surface 310 and active electrode elements 312 and 313, whereby filtered fluid elements of the blood pass into and through the capillary pores of the membrane 210 effectively to constitute a self-provided electrolyte for the ensuing polarographic reaction.

In a preferred embodiment, the anode wire 209 is composed of a silver wire approximately 0.05 inches in diameter, and the cathode wire 208 is a noble metal wire, such as of silver or gold, which has a diameter of approximately 0.004 inches. The capillary pore ultrafiltration membrane is of polycarbonate or polyester filter material with pore sizes in the range 0.01 to 0.05 micrometers and a pore density between 20 and 30 million per square centimeter. Such filtration materials are commercially available. The housing 201, sensor body 207, and membrane retaining ring 211 are of a suitably nonreactive material, such as for example polycarbonate. The heat sink 316 is brass, for free conduction of thermal energy to the thermistor in housing 321.

The foregoing has set forth preferred and illustrative embodiments of the principles of the present invention. It will be appreciated that numerous alternative embodiments will occur to those of ordinary skill in the art without departure from the spirit or the scope of the principles of the present invention. For example, one may prefer to have the female threaded aspect on the sensor assembly, and the male aspect on the cable assembly. Use of heat sealing or epoxy connections may be desirable, rather than utilizing a membrane retaining ring. Similarly, numerous other expediencies may be pursued which are well within the purview of the principles of the present invention.

We claim:

1. A polarographic sensor for monitoring or measuring partial pressure of blood oxygen comprising:
    respective anode and cathode electrode elements carried fixedly on a given surface;
    an ultrafiltration membrane directly overlying and contacting said surface and said electrode elements, said membrane defining substantially cylindrical pores having diameters of less than 12 micrometers; and
    means for passing blood over the side of said membrane not in contact with said surface.

2. An electrode as defined in claim 1 wherein said pores have diameters in the range 0.01 to 0.05 micrometers, and a density distribution in the range of 20-30 million per square centimeter.

3. An electrode as defined in claim 1 wherein said membrane consists of a film of material having a thickness between 5 and 20 micrometers and selected from the group consisting of polycarbonate and polyester.

4. An electrode as described in claim 1 wherein said membrane acts to pass and hence filter hydrous elements of the blood, which functions as an electrolyte for said electrode.

5. A sensor as described in claim 1 wherein said membrane is composed of material which hydrates in less than 10 minutes time, and which is physically, mechanically, and thermally stable when wet.

6. A sensor as described in claim 1 wherein said membrane defines up to $6 \times 10^9$ of said pores per square centimeter.

* * * * *